United States Patent [19]

Maloy

[11] Patent Number: 5,620,954
[45] Date of Patent: Apr. 15, 1997

[54] PEPTIDE COMPOSITIONS AND USES THEREFOR

[75] Inventor: W. Lee Maloy, Lansdale, Pa.

[73] Assignee: Magainin Pharmaceuticals, Inc., Plymouth Meeting, Pa.

[21] Appl. No.: 451,307

[22] Filed: May 26, 1995

Related U.S. Application Data

[63] Continuation of Ser. No. 183,725, Nov. 19, 1993, abandoned, which is a continuation of Ser. No. 681,705, Apr. 8, 1991, abandoned.

[51] Int. Cl.$^6$ ............... A61K 38/10; C07K 14/00
[52] U.S. Cl. .................. 514/12; 514/13; 514/2; 530/324; 530/325; 530/326
[58] Field of Search .................. 514/12, 13, 2; 530/324, 325, 326

[56] References Cited

U.S. PATENT DOCUMENTS

| | | | |
|---|---|---|---|
| 4,507,230 | 3/1985 | Tam et al. | 530/337 |
| 4,962,277 | 10/1990 | Cuervo et al. | 530/326 |
| 5,073,542 | 12/1991 | Zasloff | 514/12 |
| 5,114,921 | 5/1992 | Zasloff | 530/324 |
| 5,221,664 | 6/1993 | Berkowitz et al. | 530/324 |
| 5,235,038 | 8/1993 | Blondell et al. | 530/324 |
| 5,294,605 | 3/1994 | Houghten et al. | 530/324 |

*Primary Examiner*—Christina Y. Chan
*Assistant Examiner*—T. D. Wessendorf
*Attorney, Agent, or Firm*—Finnegan, Henderson, Farabow, Garrett & Dunner, L.L.P.

[57] ABSTRACT

Novel biologically active amphiphilic peptides and/or analogues or derivatives are used as a pharmaceutical. Such peptides have antibiotic and/or anti-viral and/or anti-tumor and/or anti-parasitic and/or anti-spermicidal activity.

11 Claims, No Drawings

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 26 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: amphiphilic, amide- or carboxy- terminated.

( x i ) SEQUENCE DESCRIPTION: SEQ ID NO:1:

```
Gly  Ala  Ser  Phe  Leu  Gly  Lys  Ala  Leu  Lys
                      5                           10
Ala  Ala  Leu  Lys  Ile  Gly  Ala  Asn  Leu  Leu
                     15                           20
Gly  Gly  Thr  Pro  Gln  Gln
                     25
```

( 2 ) INFORMATION FOR SEQ ID NO:2:

( i ) SEQUENCE CHARACTERISTICS:
        ( A ) LENGTH: 26 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: amphiphilic, amide- or carboxy- terminated.

( x i ) SEQUENCE DESCRIPTION: SEQ ID NO:2:

```
Gly  Phe  Ser  Phe  Leu  Gly  Lys  Ala  Leu  Lys
```

```
                                  5                              10
    Ala Ala Leu Lys Ile Gly Ala Asn Leu Leu
                     15                          20

Gly Gly Thr Pro Gln Gln
                     25
```

(2) INFORMATION FOR SEQ ID NO:3:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (ix) FEATURE:
        (D) OTHER INFORMATION: amphiphilic, amide- or
            carboxy- terminated.

(xi) SEQUENCE DESCRIPTION: SEQ ID NO:3:

```
    Gly Phe Ala Phe Leu Gly Lys Ala Leu Lys
                     5                           10

Ala Ala Leu Lys Ile Gly Ala Asn Leu Leu
                     15                          20

Gly Gly Thr Pro Gln Gln
                     25
```

(2) INFORMATION FOR SEQ ID NO:4:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (ix) FEATURE:
        (D) OTHER INFORMATION: amphiphilic, amide- or
            carboxy- terminated.

(xi) SEQUENCE DESCRIPTION: SEQ ID NO:4:

```
    Gly Phe Ala Ser Leu Gly Lys Ala Leu Lys
                     5                           10

Ala Ala Leu Lys Ile Gly Ala Asn Leu Leu
                     15                          20

Gly Gly Thr Pro Gln Gln
                     25
```

(2) INFORMATION FOR SEQ ID NO:5:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (ix) FEATURE:
        (D) OTHER INFORMATION: amphiphilic, amide- or
            carboxy- terminated.

(xi) SEQUENCE DESCRIPTION: SEQ ID NO:5:

```
    Gly Phe Ala Ser Phe Gly Lys Ala Leu Lys
                     5                           10
```

```
         Ala  Ala  Leu  Lys  Ile  Gly  Ala  Asn  Leu  Leu
                            15                           20

Gly  Gly  Thr  Pro  Gln  Gln
                            25
```

(2) INFORMATION FOR SEQ ID NO:6::

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (ix) FEATURE:
        (D) OTHER INFORMATION: amphiphilic, amide- or
            carboxy- terminated.

(xi) SEQUENCE DESCRIPTION: SEQ ID NO:6:

```
         Gly  Phe  Ala  Ser  Phe  Leu  Gly  Lys  Ala  Leu
                            5                            10

Lys  Ala  Ala  Leu  Lys  Gly  Ala  Asn  Leu  Leu
                            15                           20

Gly  Gly  Thr  Pro  Gln  Gln
                            25
```

(2) INFORMATION FOR SEQ ID NO:7:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (ix) FEATURE:
        (D) OTHER INFORMATION: amphiphilic, amide- or
            carboxy- terminated.

(xi) SEQUENCE DESCRIPTION: SEQ ID NO:7:

```
         Gly  Phe  Ala  Ser  Phe  Leu  Gly  Lys  Ala  Leu
                            5                            10

Lys  Ala  Ala  Leu  Lys  Ile  Ala  Asn  Leu  Leu
                            15                           20

Gly  Gly  Thr  Pro  Gln  Gln
                            25
```

(2) INFORMATION FOR SEQ ID NO:8:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (ix) FEATURE:
        (D) OTHER INFORMATION: amphiphilic, amide- or
            carboxy- terminated.

(xi) SEQUENCE DESCRIPTION: SEQ ID NO:8:

```
         Gly  Phe  Ala  Ser  Phe  Leu  Gly  Lys  Ala  Leu
                            5                            10

Lys  Ala  Ala  Leu  Lys  Ile  Gly  Asn  Leu  Leu
                            15                           20
```

```
        Gly Gly Thr Pro Gln Gln
                     25
```

( 2 ) INFORMATION FOR SEQ ID NO:9:

( i ) SEQUENCE CHARACTERISTICS:
        ( A ) LENGTH: 26 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: amphiphilic, amide- or
            carboxy- terminated.

( x i ) SEQUENCE DESCRIPTION: SEQ ID NO:9:

```
        Gly Phe Ala Ser Phe Leu Gly Lys Ala Leu
                         5                    10

Lys Ala Ala Leu Lys Ile Gly Ala Leu Leu
                        15                    20

Gly Gly Thr Pro Gln Gln
                     25
```

( 2 ) INFORMATION FOR SEQ ID NO:10:

( i ) SEQUENCE CHARACTERISTICS:
        ( A ) LENGTH: 26 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: amphiphilic, amide- or
            carboxy- terminated.

( x i ) SEQUENCE DESCRIPTION: SEQ ID NO:10:

```
        Gly Phe Ala Ser Phe Leu Gly Lys Ala Leu
                         5                    10

Lys Ala Ala Leu Lys Ile Gly Ala Asn Leu
                        15                    20

Gly Gly Thr Pro Gln Gln
                     25
```

( 2 ) INFORMATION FOR SEQ ID NO:11:

( i ) SEQUENCE CHARACTERISTICS:
        ( A ) LENGTH: 26 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: amphiphilic, amide- or
            carboxy- terminated.

( x i ) SEQUENCE DESCRIPTION: SEQ ID NO:11:

```
        Gly Phe Ala Ser Phe Leu Gly Lys Ala Leu
                         5                    10

Lys Ala Ala Leu Lys Ile Gly Ala Asn Leu
                        15                    20

Leu Gly Thr Pro Gln Gln
```

(2) INFORMATION FOR SEQ ID NO:12:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (ix) FEATURE:
        (D) OTHER INFORMATION: amphiphilic, amide- or
            carboxy- terminated.

(xi) SEQUENCE DESCRIPTION: SEQ ID NO:12:

Gly Phe Ala Ser Phe Leu Gly Lys Ala Leu
                5                           10

Lys Ala Ala Leu Lys Ile Gly Ala Asn Leu
                15                         20

Leu Gly Gly Pro Gln Gln
            25

(2) INFORMATION FOR SEQ ID NO:13:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (ix) FEATURE:
        (D) OTHER INFORMATION: amphiphilic, amide- or
            carboxy- terminated.

(xi) SEQUENCE DESCRIPTION: SEQ ID NO:13:

Gly Phe Ala Ser Phe Leu Gly Lys Ala Leu
                5                           10

Lys Ala Ala Leu Lys Ile Gly Ala Asn Leu
                15                         20

Leu Gly Gly Thr Gln Gln
            25

(2) INFORMATION FOR SEQ ID NO:14:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (ix) FEATURE:
        (D) OTHER INFORMATION: amphiphilic, amide- or
            carboxy- terminated.

(xi) SEQUENCE DESCRIPTION: SEQ ID NO:14:

Gly Phe Ala Ser Phe Leu Gly Lys Ala Leu
                5                           10

Lys Ala Ala Leu Lys Ile Gly Ala Asn Leu
                15                         20

Leu Gly Gly Thr Pro Gln
            25

( 2 ) INFORMATION FOR SEQ ID NO:15:

( i ) SEQUENCE CHARACTERISTICS:
        ( A ) LENGTH: 26 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: amphiphilic, amide- or carboxy- terminated.

( x i ) SEQUENCE DESCRIPTION: SEQ ID NO:15:

```
Phe  Ala  Ser  Phe  Leu  Gly  Lys  Ala  Leu  Lys
                    5                        10

Ala  Ala  Leu  Lys  Ile  Gly  Ala  Asn  Leu  Leu
                    15                       20

Gly  Gly  Thr  Pro  Gln  Gln
                    25
```

( 2 ) INFORMATION FOR SEQ ID NO:16:

( i ) SEQUENCE CHARACTERISTICS:
        ( A ) LENGTH: 27 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: amphiphilic, amide- or carboxy- terminated.

( x i ) SEQUENCE DESCRIPTION: SEQ ID NO:16:

```
Gly  Phe  Ala  Ser  Lys  Leu  Gly  Lys  Ala  Leu
                    5                        10

Lys  Ala  Ala  Leu  Lys  Ile  Gly  Ala  Asn  Leu
                    15                       20

Leu  Gly  Gly  Thr  Pro  Gln  Gln
                    25
```

( 2 ) INFORMATION FOR SEQ ID NO:17:

( i ) SEQUENCE CHARACTERISTICS:
        ( A ) LENGTH: 27 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: amphiphilic, amide- or carboxy- terminated.

( x i ) SEQUENCE DESCRIPTION: SEQ ID NO:17:

```
Gly  Phe  Gly  Ser  Lys  Leu  Gly  Lys  Ala  Leu
                    5                        10

Lys  Ala  Ala  Leu  Lys  Ile  Gly  Ala  Asn  Leu
                    15                       20

Leu  Gly  Gly  Thr  Pro  Gln  Gln
                    25
```

( 2 ) INFORMATION FOR SEQ ID NO:18:

(i) SEQUENCE CHARACTERISTICS:
  (A) LENGTH: 27 amino acids
  (B) TYPE: amino acid
  (C) STRANDEDNESS:
  (D) TOPOLOGY: linear (ii) MOLECULE TYPE: peptide (ix) FEATURE:
  (D) OTHER INFORMATION: amphiphilic, amide- or carboxy- terminated.

(xi) SEQUENCE DESCRIPTION: SEQ ID NO:18:

Gly Phe Gly Ser Phe Leu Gly Lys Ala Leu
              5                    10
Lys Ala Ala Leu Lys Ile Gly Ala Asn Met
              15                   20
Leu Gly Gly Ser Pro Gln Gln
              25

(2) INFORMATION FOR SEQ ID NO:19:

(i) SEQUENCE CHARACTERISTICS:
    (A) LENGTH: 27 amino acids
    (B) TYPE: amino acid
    (C) STRANDEDNESS:
    (D) TOPOLOGY: linear (ii) MOLECULE TYPE: peptide (ix) FEATURE:
    (D) OTHER INFORMATION: amphiphilic, amide- or carboxy- terminated.

(xi) SEQUENCE DESCRIPTION: SEQ ID NO:19:

Gly Phe Gly Ser Phe Leu Gly Lys Ala Leu
              5                    10
Lys Ala Ala Leu Lys Ile Gly Ala Asn Met
              15                   20
Leu Gly Gly Ser Leu Gln Gln
              25

(2) INFORMATION FOR SEQ ID NO:20:

(i) SEQUENCE CHARACTERISTICS:
    (A) LENGTH: 27 amino acids
    (B) TYPE: amino acid
    (C) STRANDEDNESS:
    (D) TOPOLOGY: linear (ii) MOLECULE TYPE: peptide (ix) FEATURE:
    (D) OTHER INFORMATION: amphiphilic, amide- or carboxy- terminated.

(xi) SEQUENCE DESCRIPTION: SEQ ID NO:20:

Gly Phe Gly Ser Phe Leu Gly Leu Ala Leu
              5                    10
Lys Ala Ala Leu Lys Ile Gly Ala Asn Met
              15                   20
Leu Gly Gly Ala Pro Gln Gln
              25

(2) INFORMATION FOR SEQ ID NO:21:

(i) SEQUENCE CHARACTERISTICS:

(A) LENGTH: 27 amino acids
(B) TYPE: amino acid
(C) STRANDEDNESS:
(D) TOPOLOGY: linear (ii) MOLECULE TYPE: peptide (ix) FEATURE:
(D) OTHER INFORMATION: amphiphilic, amide- or carboxy- terminated.

(xi) SEQUENCE DESCRIPTION: SEQ ID NO:21:

```
Gly Leu Ala Ser Leu Leu Gly Lys Ala Leu
                  5                   10
Lys Ala Ala Leu Lys Ile Gly Ala Asn Met
                 15                   20
Leu Gly Gly Ser Pro Gln Gln
                 25
```

(2) INFORMATION FOR SEQ ID NO:22:

(i) SEQUENCE CHARACTERISTICS:
(A) LENGTH: 27 amino acids
(B) TYPE: amino acid
(C) STRANDEDNESS:
(D) TOPOLOGY: linear (ii) MOLECULE TYPE: peptide (ix) FEATURE:
(D) OTHER INFORMATION: amphiphilic, amide- or carboxy- terminated.

(xi) SEQUENCE DESCRIPTION: SEQ ID NO:22:

```
Gly Phe Gly Ser Phe Leu Gly Lys Ala Leu
                  5                   10
Lys Ala Ala Leu Lys Ile Gly Ala Asn Leu
                 15                   20
Leu Gly Gly Thr Pro Gln Gln
                 25
```

(2) INFORMATION FOR SEQ ID NO:23:

(i) SEQUENCE CHARACTERISTICS:
(A) LENGTH: 27 amino acids
(B) TYPE: amino acid
(C) STRANDEDNESS:
(D) TOPOLOGY: linear (ii) MOLECULE TYPE: peptide (ix) FEATURE:
(D) OTHER INFORMATION: amphiphilic, amide- or carboxy- terminated.

(xi) SEQUENCE DESCRIPTION: SEQ ID NO:23:

```
Gly Phe Ala Lys Phe Leu Gly Lys Ala Leu
                  5                   10
Lys Ala Ala Leu Lys Ile Gly Ala Asn Leu
                 15                   20
Leu Gly Gly Thr Pro Gln Gln
                 25
```

(2) INFORMATION FOR SEQ ID NO:24:

(i) SEQUENCE CHARACTERISTICS:
(A) LENGTH: 27 amino acids
(B) TYPE: amino acid (C) STRANDEDNESS:
(D) TOPOLOGY: linear (ii) MOLECULE TYPE: peptide (ix) FEATURE:
    (D) OTHER INFORMATION: amphiphilic, amide- or
        carboxy- terminated.

(xi) SEQUENCE DESCRIPTION: SEQ ID NO:24:

Gly Phe Gly Lys Phe Leu Gly Lys Ala Leu
                  5                   10

Lys Ala Ala Leu Lys Ile Gly Ala Asn Leu
                15                   20

Leu Gly Gly Thr Pro Gln Gln
                25

(2) INFORMATION FOR SEQ ID NO:25:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (ix) FEATURE:
        (D) OTHER INFORMATION: amphiphilic, amide- or
            carboxy- terminated.

(xi) SEQUENCE DESCRIPTION: SEQ ID NO:25:

Gly Phe Lys Lys Phe Leu Gly Lys Ala Leu
                  5                   10

Lys Ala Ala Leu Lys Ile Gly Ala Asn Leu
                15                   20

Leu Gly Gly Thr Pro Gln Gln
                25

(2) INFORMATION FOR SEQ ID NO:26:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (ix) FEATURE:
        (D) OTHER INFORMATION: amphiphilic, amide- or
            carboxy- terminated.

(xi) SEQUENCE DESCRIPTION: SEQ ID NO:26:

Gly Leu Ala Ser Phe Leu Gly Lys Ala Leu
                  5                   10

Lys Ala Ala Leu Lys Ile Gly Ala Asn Leu
                15                   20

Leu Gly Gly Thr Pro Gln Gln
                25

(2) INFORMATION FOR SEQ ID NO:27:

(i) SEQUENCE CHARACTERISTICS:
        (A) LENGTH: 27 amino acids
        (B) TYPE: amino acid
        (C) STRANDEDNESS:
        (D) TOPOLOGY: linear (i i) MOLECULE TYPE: peptide (i x) FEATURE:
    (D) OTHER INFORMATION: amphiphilic, amide- or carboxy- terminated.

(x i) SEQUENCE DESCRIPTION: SEQ ID NO:27:

Gly Leu Ala Ser Leu Leu Gly Lys Ala Leu
                  5                   10

Lys Ala Ala Leu Lys Ile Gly Ala Asn Leu
                 15                   20

Leu Gly Gly Thr Pro Gln Gln
                 25

PEPTIDE COMPOSITIONS AND USES THEREFOR

This application is a continuation of application Ser. No. 08/183,725 filed Nov. 22, 1993, now abandoned, which is a continuation of application Ser. No. 07/681,705, filed Apr. 8, 1991, abandoned.

The present invention is related to certain novel peptides and to the use of such peptides and to compositions containing such peptides. More particularly, the present invention is directed to pharmaceutical uses and compositions of such peptides.

In accordance with an aspect of the present invention, there is provided an analogue of a biologically active amphiphilic amide or carboxy-terminated peptide, said peptide being represented by the following structural formula, and wherein the numbers below each amino acid residue refer to the position of the residue in the peptide:

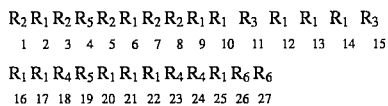

$R_1$ is a hydrophobic amino acid, $R_2$ is a hydrophobic amino acid or a basic hydrophilic amino acid, $R_3$ is a basic hydrophilic amino acid, $R_4$ is a hydrophobic or neutral hydrophilic amino acid, $R_5$ is a basic hydrophilic or a neutral hydrophilic amino acid, and $R_6$ is a neutral hydrophilic amino acid. At least one of and no more than seven of amino acid residues 2 through 26 are deleted from the peptide. In one embodiment, one of amino acid residues 2 through 26 is deleted from the peptide.

The hydrophobic amino acids are Ala, Cys, Phe, Gly, Ile, Leu, Met, Pro, Val, Trp, Tyr, norleucine (Nle), norvaline (Nval), and cyclohexylalanine (Cha).

The neutral hydrophilic amino acids are Asn, Gln, Ser, and Thr.

The basic hydrophilic amino acids are Lys, Arg, His, Orn, homoarginine (Har), and 2,4-diaminobutyric acid (Dbu).

Such analogues are sometimes hereinafter referred to as "deletion analogues." Representative examples of such deletion analogues comprise the following sequences:
(SEQ ID NO:1)
(SEQ ID NO:2)
(SEQ ID NO:3)
(SEQ ID NO:4)
(SEQ ID NO:5)
(SEQ ID NO:6)
(SEQ ID NO:7)
(SEQ ID NO:8)
(SEQ ID NO:9)
(SEQ ID NO:10)
(SEQ ID NO:11)
(SEQ ID NO:12)
(SEQ ID NO:13)
(SEQ ID NO:14)

In accordance with another aspect of the present invention, there is provided a biologically active amphiphilic peptide having the following structural formula:

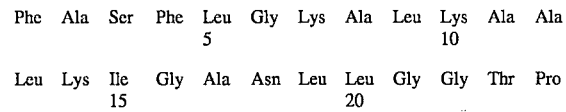

(SEQ ID NO: 15)

In accordance with another aspect of the present invention, there is provided a biologically active amphiphilic peptide which includes the following basic peptide structure x:

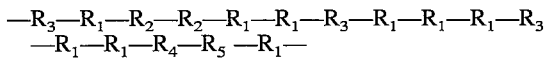

wherein $R_1$ is a hydrophobic amino acid;

$R_2$ is a hydrophobic amino acid or a basic hydrophilic amino acid;

$R_3$ is a basic hydrophilic amino acid;

$R_4$ is a hydrophobic or neutral hydrophilic amino acid; and $R_5$ is a basic or neutral hydrophilic amino acid. The hereinabove basic structure is hereinafter symbolically indicated as X.

The CPF peptide may include only the hereinabove noted amino acids or may include additional amino acids at the amino and/or carboxyl end or both the amino and carboxyl end. In general, the peptide does not include more than 40 amino acids.

The CPF peptides including the above basic structure preferably have from 1 to 4 additional amino acids at the amino end.

Accordingly, such preferred peptides may be represented by the structural formula:

Y—X— wherein X is the hereinabove described basic peptide structure and Y is (i) $R_5$—, or
(ii) $R_2$—$R_5$—; or
(iii) $R_1$—$R_2$—$R_5$; or
(iv) $R_2$—$R_1$—$R_2$—$R_5$; preferably Glycine-$R_1$—$R_2$—$R_5$.

wherein $R_1$, $R_2$ and $R_5$ are as previously defined. The carboxyl end of the basic peptide structure may also have additional amino acids which may range from 1 to 13 additional amino acids.

In a preferred embodiment, the basic structure may have from 1 to 7 additional amino acids at the carboxyl end, which may be represented as follows:

—X—Z wherein

X is the hereinabove defined basic peptide structure and Z is (i) $R_1$—, or
(ii) $R_1$—$R_1$—; or
(iii) $R_1$—$R_1$—$R_4$; or
(iv) $R_1$—$R_1$—$R_4$—$R_4$; or
(v) $R_1$—$R_1$—R4—$R_4$—$R_1$; or
(vi) $R_1$—$R_1$—$R_4$—$R_4$—$R_1$—$R_6$; or
(vii) $R_1$—$R_1$—$R_4$—R4—$R_1$—$R_6$—$R_6$, wherein $R_1$ and $R_4$ are as previously defined, and $R_6$ is a neutral hydrophilic amino acid.

Preferred peptides may be represented by the following structural formula $(Y)_a$—X—$(Z)_b$ wherein X, Y and Z are as previously defined and a is 0 or 1 and b is 0 or 1.

Representative examples of such peptides comprise the following sequences:

(SEQ ID NO:16)
(SEQ ID NO:17)

In accordance with yet another aspect of the present invention, there is provided a biologically active amphiphilic peptide selected from the class consisting of:
(SEQ ID NO:18);
(SEQ ID NO:19);
(SEQ ID NO:20);
(SEQ ID NO:21);
(SEQ ID NO:22);
(SEQ ID NO:23);
(SEQ ID NO:24);
(SEQ ID NO:25);
(SEQ ID NO:26); and
(SEQ ID NO:27).

In accordance with one embodiment, each of the amino acid residues contained in the peptides is a D-amino acid residue or glycine. Although the scope of this particular embodiment is not to be limited to any theoretical reasoning, it is believed that the above-mentioned peptides, when consisting entirely of D-amino acid or glycine residues, may have increased resistance to proteolytic enzymes while retaining their biological activity. Such peptides thus may be administered orally. Also, in accordance with another embodiment, all of the amino acid residues may be D-amino acid or glycine residues, or L-amino acid or glycine residues.

The peptides hereinabove described are ion channel forming peptides. An ion channel forming peptide or ionophore is one which increases the permeability for ions across a natural or synthetic lipid membrane. Christensen et al. PNAS Vol. 85 P. 5072–76 (July 1988) describes methodology which indicates whether or not a peptide has ion channel properties and is therefore an ionophore. As used herein an ion channel-forming peptide is a peptide which has ion channel-forming properties as determined by the method of Christensen, et al.

In general, the peptides and/or analogues or derivatives thereof are generally water soluble to a concentration of at least 20 mg/ml at neutral pH in water. In addition, the structure of such peptide provides for flexibility of the peptide molecule. When the peptide is placed in water, it does not assume an amphiphilic structure. When the peptide encounters an oily surface or membrane, the peptide chain folds upon itself into a rod-like structure.

The peptides and/or analogues or derivatives thereof may be administered to a host; for example a human or non-human animal, in an amount effective to inhibit growth of a target cell or virus. Thus, for example, the peptides and/or analogues or derivatives thereof may be used as antimicrobial agents anti-viral agents, anti-bacterial agents, anti-tumor agents, anti-parasitic agents, spermicides, as well as exhibiting other bioactive functions.

The term "antimicrobial" as used herein means that the polypeptides of in the present invention inhibit, prevent, or destroy the growth or proliferation of microbes such as bacteria, fungi, viruses, or the like.

The term "anti-bacterial" as used herein means that the polypeptides employed in the present invention produce effects adverse to the normal biological functions of bacteria, including death or destruction and prevention of the growth or proliferation of the bacteria when contacted with the polypeptides.

The term "antibiotic" as used herein means that the peptides employed in the present invention produce effects adverse to the normal biological functions of the non-host cell, tissue or organism, including death or destruction and prevention of the growth or proliferation of the non-host cell, tissue, or organism when contacted with the peptides.

The term "spermicidal" as used herein means that the polypeptides employed in the present invention, inhibit, prevent, or destroy the motility of sperm.

The term "antiviral" as used herein means that the polypeptides employed in the present invention inhibit, prevent, or destroy the growth or proliferation of viruses, or of virally-infected cells.

The term "anti-tumor" as used herein means that the polypeptide inhibits the growth of or destroys tumors.

The term "anti-parasitic" as used herein means that the polypeptides employed in the present invention inhibit, prevent, or destroy the growth or proliferation of parasites.

The peptides of the present invention have a broad range of potent antibiotic activity against a plurality of microorganisms including gram-positive and gram-negative bacteria, fungi, protozoa, and the like, as well as parasites. The peptides of the present invention allow a method for treating or controlling microbial infection caused by organisms which are sensitive to the peptides. Such treatment may comprise administering to a host organism or tissue susceptible to or affiliated with a microbial infection an antimicrobial amount of at least one of the peptides.

Because of the antibiotic, antimicrobial, antiviral, and antibacterial properties of the peptides, they may also be used as preservatives or sterilants or disinfectants of materials susceptible to microbial or viral contamination.

The peptides and/or derivatives or analogues thereof may be administered in combination with a non-toxic pharmaceutical carrier or vehicle such as a filler, non-toxic buffer, or physiological saline solution. Such pharmaceutical compositions may be used topically or systemically and may be in any suitable form such as a liquid, solid, semi-solid, injectable solution, tablet, ointment, lotion, paste, capsule, or the like. The peptide compositions may also be used in combination with adjuvants, protease inhibitors, or compatible drugs where such a combination is seen to be desirable or advantageous in controlling infection caused by harmful microorganisms including protozoa, viruses, and the like, as well as by parasites.

The peptides of the present invention may be administered to a host; in particular a human or non-human animal, in an effective antibiotic and/or anti-tumor and/or anti-viral and/or anti-microbial and/or antibacterial and/or anti-parasitic and/or an antispermicidal amount.

Depending on the use, a composition in accordance with the invention will contain an effective anti-microbial amount and/or an effective antispermicidal amount and/or an effective anti-viral amount and/or an effective anti-tumor amount and/or an effective anti-parasitic and/or an effective antibiotic amount of one or more of the hereinabove described peptides which have such activity. The peptides may be administered by direct application of the peptides to the target cell or virus or virally-infected cell, or indirectly applied through systemic administration.

The peptides of the present invention may also be employed in promoting or stimulating healing of a wound in a host.

The term "wound healing" as used herein includes various aspects of the wound healing process.

These aspects include, but are limited to, increased contraction of the wound, increased deposition of connective tissue, as evidenced by, for example, increased deposition of collagen in the wound, and increased tensile strength of the wound, i.e., the peptides increase wound breaking strength. The peptides of the present invention may also be employed so as to reverse the inhibition of wound healing caused by conditions which depress or compromise the immune system.

The peptides of the present invention may be used in the treatment of external burns and to treat and/or prevent skin and burn infections. In particular, the peptides may be used to treat skin and burn infections caused by organisms such as, but not limited to, *P. aeruginosa* and *S. aureus*.

The peptides are also useful in the prevention or treatment of eye infections. Such infections may be caused by bacteria such as, but not limited to, *P. aeruginosa, S. aureus*, and *N. gonorrhoeae*, by fungi such as but not limited to *C. albicans* and *A. fumigatus*, by parasites such as but not limited to *A. castellani*, or by viruses.

The peptides may also be effective in killing cysts, spores, or trophozoites of infection—causing organisms. Such organisms include, but are not limited to *Acanthamoeba* which forms trophozoites or cysts, *C. albicans*, which forms spores, and *A. fumigatus*, which forms spores as well.

The peptides may also be administered to plants in an effective antimicrobial or antiviral or antiparasitic amount to prevent or treat microbial or viral or parasitic contamination thereof.

The peptides, when used in topical compositions, are generally present in an amount of at least 0.1%, by weight. In most cases, it is not necessary to employ the peptide in an amount greater than 1.0%, by weight.

In employing such compositions systemically (intramuscular, intravenous, intraperitoneal), the active peptide is present in an amount to achieve a serum level of the peptide of at least about 5 ug/ml. In general, the serum level of peptide need not exceed 500 ug/ml. A preferred serum level is about 100 ug/ml. Such serum levels may be achieved by incorporating the peptide in a composition to be administered systemically at a dose of from 1 to about 10 mg/kg. In general, the peptide(s) need not be administered at a dose exceeding 100 mg/kg.

The peptides may be produced by known techniques and obtained in substantially pure form. For example, the peptides may be synthesized on an automatic peptide synthesizer. *Journal of the American Chemical Society*, Vol. 85, pgs. 2149–54 (1963). It is also possible to produce such peptides by genetic engineering techniques.

In accordance with another embodiment, the peptides of the present invention may be employed in combination with a toxic ion for the purposes hereinabove described.

A toxic ion is one which when introduced into a target cell inhibits and/or prevents and/or destroys the growth of the target cell.

Such a toxic ion is one which in the absence of an ion channel forming peptide is unable to cross a natural or synthetic lipid membrane; in particular a cell membrane, in sufficient amounts to affect a cell adversely.

The peptide and toxic ion may be administered as a single composition or in separate compositions, and the single or separate compositions may include additional materials, actives and/or inactives, in addition to the peptide and toxic ion. As representative examples of toxic ions which may be employed, there may be mentioned fluoride, peroxide, bicarbonate, silver, zinc, mercury, arsenic, copper, platinum, antimony, gold, thallium, nickel, selenium, bismuth, and cadmium ions.

The peptide and the toxic ion, whether administered or prepared in a single composition or in separate compositions, are employed in amounts effective to inhibit and/or prevent and/or destroy the growth of the target cell. In effect, the ion potentiates the action of the peptide, i.e., the amount of toxic ion is effective to reduce the maximum effective concentration of the peptide or protein for inhibiting growth of a target cell.

The toxic ion, when used topically, is generally employed in a concentration of from 0.05% to 2.0%. When used systemically, the ion is generally employed in an amount of from 1 to 10 mg. per kg. of host weight. Peptide dosages may be within the ranges hereinabove described.

It is also to be understood that the peptide and toxic ion may be delivered or administered in different forms; for example, the toxic ion may be administered orally, while the peptide may be administered by IV or IP.

As representative examples of administering the peptide or protein and toxic ion for topical or local administration, the peptide could be administered in an amount of up to about 1% weight to weight and the toxic ion delivered in an amount of about 50 mM (about 0.1%). Alternatively, the toxic ion, in the form of a salt such as sodium fluoride, could be administered orally in conjunction with systemic administration of the peptide. For example, the peptide may be administered IV or IP to achieve a serum dose of 100 micrograms per milliliter (10 milligrams per kilogram) in conjunction with an oral dose of toxic ion, in particular, sodium fluoride, of 10 meq per kilogram.

In accordance with another embodiment, the peptides of the present invention may be administered to a host in combination with an antibiotic selected from the class consisting of bacitracins, gramacidin, polymyxin, vancomycin, teichoplanin, aminoglycosides, hydrophobic antibiotics, penicillins, monobactams, or derivatives or analogues thereof.

The bacitracins, gramacidin, polymyxin, vancomycin, teichoplanin, and derivatives and analogues thereof, are a group of polypeptide antibiotics. A preferred bacitracin is bacitracin A.

Aminoglycoside antibiotics include tobramycin, kanamycin, amikacin, the gentamicins (e.g., gentamicin $C_1$, gentamicin $C_2$, gentamicin $C_{1a}$), netilmicin, kanamycin, and derivatives and analogues thereof. The preferred aminoglycosides are tobramycin and the gentamicins. The aminoglycosides, and the bacitracins hereinabove described, tend to be hydrophilic and water-soluble.

Penicillins which may be employed include, but are not limited to benzyl penicillin, ampicillin, methicillin (dimethoxyphenyl penicillin), ticaricillin, penicillin V (phenoxymethyl penicillin), oxacillin, cloxacillin, dicloxacillin, flucloxacillin, amoxicillin, and amidinocillin. Preferred penicillins which may be employed are benzyl penicillin and ampicillin. A preferred monobactam which may be employed is aztreonam.

As representative examples of hydrophobic antibiotics which may be used in the present invention, there may be mentioned macrolides such as erythromycin, roxythromycin, clarithromycin, etc.; 9-N-alkyl derivatives of erythromycin; midecamycin acetate; azithromycin; flurithromycin; rifabutin; rokitamycin; a 6-O-methyl erythromycin A known as TE-031 (Taisho); rifapentine; benzypiperazinyl rifamycins such as CGP-7040, CGP-5909, CGP-279353 (Ciba-Geigy); an erythromycin A derivative with a cyclic carbamate fused to the $C_{11}/C_{12}$ position of a macrolide ring known as A-62514 (Abbott); AC-7230 (Toyo Jozo); benzoxazinorifamycin; difficidin; dirithromycin; a 3-N-piperdinomethylzaino methyl rifamycin SV known as FCE-22250 (Farmitalia); M-119-a (Kirin Brewery); a 6-O-methyl-1-4"-O-carbamoyl erythromycin known as A-63075 (Abbott); 3-formylrifamycin SV-hydrazones with diazabicycloalkyl side chains such as CGP-27557 and CGP-2986 (Ciba-Geigy); and 16-membered macrolides having a 3-O-alpha-L-cladinosyl moiety, such as 3-O-alpha-L-cladinosyldeepoxy rosaramicin; tylosins and acyl demycinosyl tylosins.

In addition to the macrolides hereinabove described, rifamycin, carbenicillin, and nafcillin may be employed as well.

Other antibiotics which may be used (whether or not hydrophobic) are antibiotics which are 50-S ribosome inhibitors such as lincomycin; clindamycin; and chloramphenicol; etc.; antibiotics which have a large lipid like lactone ring, such as mystatin; pimaricin, etc.

The peptide and antibiotic may be adminstered by direct administration to a target cell or by systemic or topical administration to a host which includes the target cell, in order to prevent, destroy or inhibit the growth of a target cell. Target cells whose growth may be prevented, inhibited, or destroyed by the administration of the peptides and antibiotic include Gram-positive and Gram-negative bacteria as well as fungal cells.

The antibiotic, such as those hereinabove described, or derivatives or analogues thereof, when used topically, is generally employed in a concentration of about 0.1% to about 10%. When used systemically, the antibiotic or derivative or analogue thereof is generally employed in an amount of from 1.25 mg. to about 45 mg. per kg. of host weight per day. Peptide dosages may be those as hereinabove described.

As representative exmples of administering the peptide and antibiotic for topical or local administration, the peptide could be administered in an amount of from about 0.1% to about 10% weight to weight, and the antibiotic is delivered in an amount of from about 0.1% to about 10% weight to weight.

In accordance with another embodiment, the peptides of the present invention may be administered in combination with an antiparasitic agent or an antifungal agent.

Antiparasitic agents which may be employed include, but are not limited to, anti-protozoan agents. Examples of specific anti-parasitic agents which may be employed include, but are not limited to, pentamidine isethionate, and propamidine isethionate (Brolene).

Anti-fungal agents which may be employed include, but are not limited to, ketoconazole. It is also to be understood that certain anti-parasitic agents, may also have anti-fungal activity, and that certain anti-fungal agents may have anti-parasitic activity.

In accordance with another embodiment, the peptides of the present invention may be administered in combination with an antibiotic which inhibits DNA gyrase, which is an enzyme involved in the formation of bonds between individual coiling strands of replicating bacterial DNA. Thus, DNA gyrase is necessary for the normal replication of bacterial DNA, and, therefore, antibiotics which inhibit DNA gyrase inhibit the normal replication of bacterial DNA.

Examples of antibiotics which inhibit DNA gyrase include nalidixic acid, oxolinic acid, cinoxacin, and quinolone antibiotics which include ciprofloxacin, norfloxacin, ofloxacin, enoxacin, pefloxacin, lomefloxacin, fleroxacin, tosulfloxacin, temafloxacin, and rufloxacin.

In accordance with another embodiment, the peptides of the present invention may be administered for the purpose hereinabove described in combination with other biologically active amphiphilic peptides, or in combination with ion channel-forming proteins.

The present invention will be further described with respect to the following example; however, the scope of the invention is not to be limited thereby.

EXAMPLE

Table I, which follows, indicates the Minimal Inhibitory Concentration (MIC) in µg/ml of Peptides (SEQ ID NO:1) through (SEQ ID NO:27) against *S. aureus* strain ATCC 25923, *P. aeruginosa* strain ATCC 27853, and *E.coli* ATCC strain 25922.

TABLE I

| Peptide | Activity (µg/ml) | | |
|---|---|---|---|
| | S. aureus | P. aeruginosa | E. coli |
| (SEQ ID NO: 1) | 16,32 | 32,64 | 16 |
| (SEQ ID NO: 2) | 16 | 64 | 16 |
| (SEQ ID NO: 3) | 16 | 64 | 16 |
| (SEQ ID NO: 4) | 64 | 128 | 32 |
| (SEQ ID NO: 5) | 64 | 128,256 | 32 |
| (SEQ ID NO: 6) | 32,64 | 128 | 32 |
| (SEQ ID NO: 7) | 16 | 32 | 8 |
| (SEQ ID NO: 8) | 16 | 32 | 16 |
| (SEQ ID NO: 9) | 16,32 | 64 | 8 |
| (SEQ ID NO: 10) | 32 | 128 | 16,32 |
| (SEQ ID NO: 11) | 16 | 64 | 8 |
| (SEQ ID NO: 12) | 8 | 32 | 8,16 |
| (SEQ ID NO: 13) | 8,16 | 32 | 8,16 |
| (SEQ ID NO: 14) | 8,16 | 64 | 8,16 |
| (SEQ ID NO: 15) | 16 | 32 | 4 |
| (SEQ ID NO: 16) | 16 | 64,128 | 8,16 |
| (SEQ ID NO: 17) | 32 | 64,128 | 8,16 |
| (SEQ ID NO: 18) | 64 | 32,64 | 32 |
| (SEQ ID NO: 19) | 32,64 | 32,64 | 8,16 |
| (SEQ ID NO: 20) | 256,>256 | >256 | >256 |
| (SEQ ID NO: 21) | 64 | 128 | 32 |
| (SEQ ID NO: 22) | 16 | 16,32 | 8,16 |
| (SEQ ID NO: 23) | 8 | 8,16 | 4,8 |
| (SEQ ID NO: 24) | 8 | 16 | 8,16 |
| (SEQ ID NO: 25) | 8,16 | 32 | 8,32 |
| (SEQ ID NO: 26) | 16,32 | 64,128 | 8,16 |
| (SEQ ID NO: 27) | 32 | 128 | 32 |

(Legend) The procedure for the antibacterial assay is based upon the guidelines of the National Committee for Clinical Laboratory Standards, Document M7-T2, Volume 8, No. 8, 1988.

Stock solutions of the hereinabove described peptides in accordance with the present invention are prepared at a concentration of 512 µg/ml in sterile deionized distilled water and stored at −70° C.

The stock peptide solution is diluted in serial dilutions (1:2) down the wells of a microtiter plate so that the final concentrations of peptides in the wells are 0.25, 0.50, 1, 2, 4, 8, 16, 32, 64, 128, and 256 µg/ml. 1–5×10$^5$ CFUs/ml of either *S. aureus* ATCC 25923, *E. coli* ATCC 25922, or *P. aeruginosa* ATCC 27853 were added to the wells in full strength Mueller Hinton broth (BBL 11443) from a mid-log culture. The inoculum is standardized spectrophotometrically at 600 nm and is verified by colony counts. The plates are incubated for 16–20 hours at 37° C., and the minimal inhibitory concentration (MIC) for each peptide is determined. Minimal inhibitory concentration is defined as the lowest concentration of peptide which produces a clear well in the microtiter plate.

The peptides of the present invention, whether administered alone or in combination with agents such as toxic ions, antibiotics, or other biologically active peptides or proteins as hereinabove described, may be employed in a wide variety of pharmaceutical compositions in combination with a non-toxic pharmaceutical carrier or vehicle such as a filler, non-toxic buffer, or physiological saline solution. Such pharmaceutical compositions may be used topically or systemically and may be in any suitable form such as a liquid, solid, semi-solid, injectable solution, tablet, ointment, lotion, paste, capsule or the like. The peptide and/or agent as hereinabove described may also be used in combination with adjuvants, protease inhibitors, or compatible drugs where such a combination is seen to be desirable or advantageous in controlling infection caused by harmful microorganisms including protozoa, viruses, parasites, fungi, and the like.

The peptide may be administered to a host in particular an animal, in an effective antibiotic and/or anti-tumor and/or antiviral and/or antimicrobial and/or antispermicidal and/or antifungal and/or antiparasitic amount, or in an amount effective to stimulate wound healing in a host. The peptides may be administered either alone or in combination with a toxic ion, antibiotic, or ion channel forming peptide or protein as hereinabove described. When the peptide is administered in combination with a toxic ion, the activity of the peptide is potentiated.

When the peptide is administered in combination with an agent as hereinabove described, it is possible to administer the peptide and agent in separate forms. For example, the agent may be administered systemically and the peptide may be administered topically.

When the peptide is administered topically, it may be administered in combination with a water-soluble vehicle, said water-soluble vehicle being in the form of an ointment, cream, lotion, paste or the like. Examples of water-soluble vehicles which may be employed include, but are not limited to, glycols, such as polyethylene glycol, hydroxycellulose, and KY Jelly. The water-soluble vehicle is preferably free of an oily substance.

The peptide may also be employed in combination with a toxic ion as hereinabove described in the form of an oral composition for oral hygiene. Such a composition may be incorporated into a wide variety of compositions and materials used for oral hygiene purposes, which include, but are not limited to, toothpastes, mouthwashes, tooth gels, and tooth powders. Such composition may thus be used to treat or prevent periodontal disease, to prevent or reduce plaque, and/or to prevent or treat or reduce dental caries. The peptide and toxic ion may be used to inhibit, prevent, or destroy the growth of *Streptococcus mutans*, which is associated with dental caries and periodontal disease.

Numerous modifications and variations of the present invention are possible in light of the above teachings; therefore, within the scope of the appended claims the invention may be practiced otherwise than as particularly described.

What is claimed is:

1. A pharmaceutical composition comprising a pharmaceutically effective amount of
   a) a biologically active amphiphilic amide- or carboxy-terminated peptide having the following structural formula:

(SEQ ID NO: 3);

and b) a non-toxic pharmaceutical carrier.

2. A pharmaceutical composition comprising a pharmaceutically effective amount of
   a) a biologically active amphiphilic amide- or carboxy-terminated peptide having the following structural formula:

(SEQ ID NO: 4);

and b) a non-toxic pharmaceutical carrier.

3. A pharmaceutical composition comprising a pharmaceutically effective amount of
   a) a biologically active amphiphilic amide- or carboxy-terminated peptide having the following structural formula:

(SEQ ID NO: 5);

and b) a non-toxic pharmaceutical carrier.

4. A pharmaceutical composition comprising a pharmaceutically effective amount of
   a) a biologically active amphiphilic amide- or carboxy-terminated peptide having the following structural formula:

(SEQ ID NO: 6);

and b) a non-toxic pharmaceutical carrier.

5. A pharmaceutical composition comprising a pharmaceutically effective amount of
   a) a biologically active amphiphilic amide- or carboxy-terminated peptide having the following structural formula:

(SEQ ID NO: 7);

and b) a non-toxic pharmaceutical carrier.

6. A pharmaceutical composition comprising a pharmaceutically effective amount of
   a) a biologically active amphiphilic amide- or carboxy-terminated peptide having the following structural formula:

(SEQ ID NO: 8);

and b) a non-toxic pharmaceutical carrier.

7. A pharmaceutical composition comprising a pharmaceutically effective amount of
   a) a biologically active amphiphilic amide- or carboxy-terminated peptide having the following structural formula:

(SEQ ID NO: 9);

and b) a non-toxic pharmaceutical carrier.

8. A pharmaceutical composition comprising a pharmaceutically effective amount of
   a) a biologically active amphiphilic amide- or carboxy-terminated peptide having the following structural formula:

(SEQ ID NO: 10);

and b) a non-toxic pharmaceutical carrier.

9. A pharmaceutical composition comprising a pharmaceutically effective amount of
   a) a biologically active amphiphilic amide- or carboxy-terminated peptide having the following structural formula:

(SEQ ID NO: 11);

and b) a non-toxic pharmaceutical carrier.

10. A pharmaceutical composition comprising a pharmaceutically effective amount of a) a biologically active amphiphilic amide- or carboxy-terminated peptide having the following structural formula:

(SEQ ID NO: 12);

and b) a non-toxic pharmaceutical carrier.

11. A pharmaceutical composition comprising a pharmaceutically effective amount of a) a biologically active amphiphilic amide- or carboxy-terminated peptide having the following structural formula:

(SEQ ID NO: 13);

and b) a non-toxic pharmaceutical carrier.

* * * * *